(12) United States Patent
Wallace et al.

(10) Patent No.: US 7,295,875 B2
(45) Date of Patent: Nov. 13, 2007

(54) METHOD OF STIMULATING/SENSING BRAIN WITH COMBINATION OF INTRAVASCULARLY AND NON-VASCULARLY DELIVERED LEADS

(75) Inventors: Michael P. Wallace, Fremont, CA (US); Robert J. Garabedian, Mountain View, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 460 days.

(21) Appl. No.: 10/783,679

(22) Filed: Feb. 20, 2004

(65) Prior Publication Data

US 2005/0187589 A1 Aug. 25, 2005

(51) Int. Cl.
*A61N 1/36* (2006.01)
(52) U.S. Cl. .......................................... 607/45; 600/378
(58) Field of Classification Search .................... 607/1, 607/2, 45, 116; 600/378, 898
See application file for complete search history.

(56) References Cited

U.S. PATENT DOCUMENTS

| | | |
|---|---|---|
| 4,141,365 A | 2/1979 | Fischell et al. |
| 4,285,347 A | 8/1981 | Hess |
| 4,519,403 A | 5/1985 | Dickhudt |
| 4,608,985 A | 9/1986 | Crish et al. |
| 4,658,835 A | 4/1987 | Pohndorf |
| 4,739,768 A | 4/1988 | Engelson |
| 4,813,934 A | 3/1989 | Engelson et al. |
| 4,869,255 A | 9/1989 | Putz |
| 4,884,579 A | 12/1989 | Engelson |
| 5,005,587 A | 4/1991 | Scott |
| 5,010,894 A | 4/1991 | Edhag |
| 5,170,802 A | 12/1992 | Mehra |
| 5,224,491 A | 7/1993 | Mehra |
| 5,234,437 A | 8/1993 | Sepetka |
| 5,239,999 A | 8/1993 | Imran |
| 5,250,071 A | 10/1993 | Palermo |
| 5,261,916 A | 11/1993 | Engelson |

(Continued)

FOREIGN PATENT DOCUMENTS

EP 0 861 676 9/1998

(Continued)

OTHER PUBLICATIONS

Kunieda, et al "Use of Cavernous Sinus EEG in the Detection of Seizure Onset and Spread in Mesial Temporal Lobe Epilepsy", Epilepsia, 41(11): 1411-1419, 2000.

(Continued)

*Primary Examiner*—George R. Evanisko
*Assistant Examiner*—Rex Holmes
(74) *Attorney, Agent, or Firm*—Vista IP Law Group LLP

(57) ABSTRACT

A method of treating a neurological disorder in a patient is provided. The method comprises intravascularly delivering a first electrical lead within the head of the patient, and non-vascularly delivering a second electrical lead within the head the patient. The vascular and intravascular leads are placed adjacent brain tissue (e.g., cortical brain tissue or deep brain tissue). Optionally, the method comprises implanting a source of stimulation and/or recorder within the patient's body, and then electrically coupling the proximal ends of the electrical leads to the implanted device. Using the electrical leads, the brain tissue can then be stimulated and/or recorded in order to treat the neurological disorder.

30 Claims, 2 Drawing Sheets

U.S. PATENT DOCUMENTS

| | | | |
|---|---|---|---|
| 5,263,488 A | 11/1993 | Van Veen et al. | |
| 5,304,195 A | 4/1994 | Twyford et al. | |
| 5,312,415 A | 5/1994 | Palermo | |
| 5,350,397 A | 9/1994 | Palermo et al. | |
| 5,365,926 A | 11/1994 | Desai | |
| 5,391,200 A | 2/1995 | KenKnight et al. | |
| 5,397,341 A | 3/1995 | Hirschberg et al. | |
| 5,411,551 A | 5/1995 | Winston et al. | |
| 5,417,719 A | 5/1995 | Hull et al. | |
| 5,423,864 A | 6/1995 | Ljungstroem | |
| 5,501,703 A | 3/1996 | Holsheimer et al. | |
| 5,509,411 A | 4/1996 | Littmann et al. | |
| 5,531,779 A | 7/1996 | Dahl et al. | |
| 5,534,007 A | 7/1996 | St. Germain et al. | |
| 5,543,864 A | 8/1996 | Hirschman et al. | |
| 5,603,731 A | 2/1997 | Whitney | |
| 5,647,870 A | 7/1997 | Kordis et al. | |
| 5,683,422 A | 11/1997 | Rise | |
| 5,702,438 A | 12/1997 | Avitall | |
| 5,707,354 A | 1/1998 | Salmon et al. | |
| 5,713,922 A | 2/1998 | King | |
| 5,716,377 A | 2/1998 | Rise et al. | |
| 5,752,979 A | 5/1998 | Benabid | |
| 5,792,187 A | 8/1998 | Adams | |
| 5,800,474 A | 9/1998 | Benabid et al. | |
| 5,814,062 A | 9/1998 | Sepetka et al. | |
| 5,833,709 A | 11/1998 | Rise et al. | |
| 5,846,238 A | 12/1998 | Jackson et al. | |
| 5,860,974 A | 1/1999 | Abele | |
| 5,871,483 A | 2/1999 | Jackson et al. | |
| 5,891,136 A | 4/1999 | McGee et al. | |
| 5,902,236 A | 5/1999 | Iversen | |
| 5,908,385 A | 6/1999 | Chechelski et al. | |
| 5,925,070 A | 7/1999 | King et al. | |
| 5,938,689 A | 8/1999 | Fischell et al. | |
| 5,954,761 A | 9/1999 | Machek et al. | |
| 5,967,986 A | 10/1999 | Cimochowski et al. | |
| 6,006,134 A | 12/1999 | Hill et al. | |
| 6,015,387 A | 1/2000 | Schwartz et al. | |
| 6,016,449 A | 1/2000 | Fischell et al. | |
| 6,018,682 A | 1/2000 | Rise | |
| 6,027,456 A | 2/2000 | Feler et al. | |
| 6,053,873 A | 4/2000 | Govari et al. | |
| 6,066,163 A | 5/2000 | John | |
| 6,074,407 A | 6/2000 | Levine et al. | |
| 6,074,507 A | 6/2000 | Sukenik | |
| 6,091,980 A | 7/2000 | Squire et al. | |
| 6,094,596 A | 7/2000 | Morgan | |
| 6,119,044 A | 9/2000 | Kuzma | |
| 6,122,548 A | 9/2000 | Starkebaum et al. | |
| 6,128,538 A | 10/2000 | Fischell et al. | |
| 6,136,021 A | 10/2000 | Tockman et al. | |
| 6,141,576 A | 10/2000 | Littmann et al. | |
| 6,161,029 A | 12/2000 | Spreigl et al. | |
| 6,161,047 A | 12/2000 | King et al. | |
| 6,170,488 B1 | 1/2001 | Spillman, Jr. et al. | |
| 6,179,858 B1 | 1/2001 | Squire et al. | |
| 6,205,361 B1 | 3/2001 | Kuzma et al. | |
| 6,216,045 B1 | 4/2001 | Black et al. | |
| 6,231,516 B1 | 5/2001 | Keilman et al. | |
| 6,249,707 B1 | 6/2001 | Kohnen et al. | |
| 6,263,248 B1 | 7/2001 | Farley et al. | |
| 6,266,568 B1 | 7/2001 | Mann et al. | |
| 6,319,251 B1 | 11/2001 | Tu et al. | |
| 6,330,477 B1 | 12/2001 | Casavant | |
| 6,353,762 B1 | 3/2002 | Baudino et al. | |
| 6,360,122 B1 | 3/2002 | Fischell et al. | |
| 6,361,528 B1 | 3/2002 | Wilson et al. | |
| 6,370,427 B1 | 4/2002 | Alt et al. | |
| 6,391,052 B2 | 5/2002 | Buirge et al. | |
| 6,393,325 B1 | 5/2002 | Mann et al. | |
| 6,397,109 B1 | 5/2002 | Cammilli et al. | |
| 6,402,746 B1 | 6/2002 | Whayne et al. | |
| 6,408,214 B1 | 6/2002 | Williams et al. | |
| 6,415,187 B1 | 7/2002 | Kuzma et al. | |
| 6,418,344 B1 | 7/2002 | Rezai et al. | |
| 6,438,427 B1 | 8/2002 | Rexhausen et al. | |
| 6,442,413 B1 | 8/2002 | Silver | |
| 6,442,435 B2 | 8/2002 | King et al. | |
| 6,445,953 B1 | 9/2002 | Bulkes et al. | |
| 6,463,328 B1 | 10/2002 | John | |
| 6,466,822 B1 | 10/2002 | Pless | |
| 6,480,743 B1 | 11/2002 | Kirkpatrick et al. | |
| 6,484,059 B2 | 11/2002 | Gielen | |
| 6,516,227 B1 | 2/2003 | Meadows et al. | |
| 6,519,488 B2 | 2/2003 | KenKnight et al. | |
| 6,522,932 B1 | 2/2003 | Kuzma et al. | |
| 6,529,774 B1 | 3/2003 | Greene | |
| 6,539,263 B1 | 3/2003 | Schiff et al. | |
| 6,547,788 B1 | 4/2003 | Maguire et al. | |
| 6,547,870 B1 | 4/2003 | Griessmann et al. | |
| 6,562,063 B1 | 5/2003 | Euteneuer et al. | |
| 6,584,358 B2 | 6/2003 | Carter et al. | |
| 6,587,733 B1 | 7/2003 | Cross, Jr. et al. | |
| 6,589,230 B2 | 7/2003 | Gia et al. | |
| 6,591,138 B1 | 7/2003 | Fischell et al. | |
| 6,597,953 B2 * | 7/2003 | Boling | 607/45 |
| 6,600,954 B2 | 7/2003 | Cohen et al. | |
| 6,606,521 B2 | 8/2003 | Paspa et al. | |
| 6,647,296 B2 | 11/2003 | Fischell et al. | |
| 6,658,302 B1 | 12/2003 | Kuzma et al. | |
| 6,662,055 B1 | 12/2003 | Prutchi | |
| 6,665,562 B2 | 12/2003 | Gluckman et al. | |
| 6,690,974 B2 | 2/2004 | Archer et al. | |
| 6,842,648 B2 | 1/2005 | Partridge et al. | |
| 6,895,283 B2 | 5/2005 | Erickson et al. | |
| 2001/0025192 A1 | 9/2001 | Gerber et al. | |
| 2001/0041821 A1 | 11/2001 | Wilk | |
| 2001/0053885 A1 | 12/2001 | Gielen et al. | |
| 2002/0111661 A1 | 8/2002 | Cross, Jr. et al. | |
| 2002/0151948 A1 | 10/2002 | King et al. | |
| 2002/0151949 A1 | 10/2002 | Dahl et al. | |
| 2002/0188207 A1 | 12/2002 | Richter | |
| 2003/0014016 A1 | 1/2003 | Purdy | |
| 2003/0040785 A1 | 2/2003 | Maschino et al. | |
| 2003/0199962 A1 | 10/2003 | Struble et al. | |
| 2003/0204135 A1 | 10/2003 | Bystritsky | |
| 2003/0204228 A1 | 10/2003 | Cross, Jr. et al. | |
| 2004/0015193 A1 | 1/2004 | Lamson et al. | |
| 2005/0137646 A1 | 6/2005 | Wallace et al. | |

FOREIGN PATENT DOCUMENTS

| | | |
|---|---|---|
| EP | 0 865 800 A2 | 9/1998 |
| EP | 0 865 800 A3 | 12/1999 |
| EP | 0 864 800 B1 | 9/2004 |
| WO | WO 01/85094 | 11/2001 |
| WO | WO 03/077986 | 9/2003 |

OTHER PUBLICATIONS

Canavero, et al "Extradural Motor Cortex Stimulation for Advanced Parkinson Disease" J. Neurosurg 97: 1208-1211, 2002.

Cagatay, et al "Complications of Invasive Subdural Grid Monitoring in Children with Epilepsy" J. Neurosurg 98: 1017-1026, 2003.

IP.com: Electrotrode Design to Stimulate Blood Vessels, Nerves, or Other Tubular Organs, file://C:\unzipped\IPCOM000010247D1\0_properties.xml, Published Nov. 13, 2002.

IP.com: Epidural Needle for Spinal Cord Stimulation Electrode, file://C:\unzipped\IPCOM000011384D1\0_properties.xml, Published Feb. 14, 2003.

IP.com: Medical Lead System and Method for Insertion into the Spinal Cord, file://C:\unzipped\IPCOM000011389D1\0_properties.xml, Published Feb. 17, 2003.

IP.com: Transcutaneous Screening Test for Evaluation of Potential Efficacy of Chronic Trigeminal Neurostimulation as a Therapy for Epilepsy, file://C:\unzipped\IPCOM000011987D1\0_properties.xml, Published Mar. 28, 2003.

IP.com: System and Method for Lead Fixation, file://C:\unzipped\IPCOM000019571D1\0_properties.xml, Published Sep. 19, 2003.

IP.com: Dual Lumen Inflatable Lead, file://C:\unzipped\IPCOM000019703D1\0_properties.xml, Published Sep. 25, 2003.

IP.com: Skull-Mounted Electrical Stimulation System, file://C:\unzipped\IPCOM000019827D1\0_properties.xml, Published Oct. 1, 2003.

IP.com: Spinal cord Stimulation as a Therapy for Epilepsy, file://C:\unzipped\IPCOM000019881D1\0_properties.xml, Published Oct. 6, 2003.

IP.com: Skull-Mounted Electrical Stimulation System and Method for Treating Patients, file://C:\unzipped\IPCOM000021554D1\0_properties.xml, Published Jan. 22, 2004.

IPCOM000012135D; IP.com: Methods of Place of Neurostimulation Lead, Infusion Catheter, and/or Sensor Via the Vasculature to the Brain.

PCT International Search Report for PCT/US2005/006569, Applicant: Boston Scientific Scimed, Inc., Forms PCT/ISA 210 and 220, dated Jun. 13, 2005 (7 pages).

PCT Written Opinion of the International Search Authority for PCT/US2005/006569, Applicant: Boston Scientific Scimed, Inc., Form PCT/ISA/237, dated Jun. 13, 2005 (5 pages).

PCT International Search Report for PCT/US2005/010121, Applicant: Boston Scientific Scimed, Inc., Forms PCT/ISA/210 and 220, dated Jul. 4, 2005 (7 pages).

PCT Written Opinion of the International Search Authority for PCT/US2005/010121, Applicant: Boston Scientific Scimed, Inc., Form PCT/ISA/237, dated Jul. 4, 2005 (5 pages).

Web Article: IP.com: "Methods and Placement of Neurostimulation Lead, Infusion Catheter, and/or Sensor Via the Vasculature to the Brain." IPCOM000012135D, Published Apr. 10, 2003 (11 pages).

Web Article: IP.com: "Methods of Placement of Neurostimulation Lead, Infusion Catheter, and/or Sensor Via Peripheral Vasculature." 0349945-003 (7 pages).

* cited by examiner

METHOD OF STIMULATING/SENSING BRAIN WITH COMBINATION OF INTRAVASCULARLY AND NON-VASCULARLY DELIVERED LEADS

FIELD OF THE INVENTION

The invention relates to the treatment and diagnosis of diseases, and in particular, the treatment and diagnosis of brain diseases using electrical leads.

BACKGROUND OF THE INVENTION

It is known to treat neurodegenerative diseases, such as Alzheimer's Disease, Parkinson's Disease, Tremor, and Epilepsy, and ischemia of the brain, such as stroke, by electrically stimulating selected portions of the brain. Currently, this is accomplished by first drilling a burr hole through the patient's cranium in order to gain access to the brain tissue. A stimulation lead, and in particular, a lead with multiple electrodes extending along its length, is then introduced through one or more burr holes into contact with the selected brain tissue. In a deep brain stimulation (DBS) procedure, typically used to treat Parkinson's Disease, Tremor, and Epilepsy, the stimulation lead is advanced through a burr hole deep into the brain, e.g., the anterior thalamus, ventrolateral thalamus (Thal), internal segment of globus pallidus (GPi), substantia nigra pars reticulata (SNr), subthalamic nucleus (STN), external segment of globus pallidus (GPe), and neostriatum. In a cortical brain stimulation procedure, typically used to rehabilitate stroke victims, the lead is introduced through two burr holes and placed underneath the dura matter in contact with the cortex of the brain.

Once the lead is properly located in contact with the selected brain tissue, the proximal end of the lead or an extension lead is subcutaneously routed from the burr hole underneath the patient's scalp, down the neck, and into the chest region in electrical connection with an implanted electrical stimulator. The electrical stimulator is programmed either prior to or after the procedure to deliver electrical pulses to the brain tissue via the stimulation lead. In some cases, it is desirable to implant sensing leads, which may be separate from or the same as the stimulation leads, within the brain. For example, it is sometimes desirable to measure cortical EEG signals using cortical leads in order to predict the onset of an epileptic seizure.

As described in U.S. patent application Ser. No. 10/744, 319, entitled "Method of Intravascularly Delivering Stimulation Leads into Brain," electrical stimulation leads can be intravascularly introduced through the cerebral blood vessels to provide a minimally invasive manner of therapeutically stimulating the brain tissue.

If a single region of the brain is to be stimulated and/or sensed, one can typically select the most efficient and safe technique of introducing the lead(s) into the brain, whether it be through a burr hole to provide access to the cortical or deep brain regions or intravascularly. It is sometimes desirable, however, to stimulate and/or sense multiple regions in the brain, in which case, there may not be a single optimum method of introducing leads into the brain.

Thus, there remains a need to provide improved methods for therapeutically stimulating brain tissue.

SUMMARY OF THE INVENTION

In accordance with the present invention, a method of performing a medical procedure on a patient is provided. For example, the patient may have a neurological disorder, in which case the method can be used to treat the disorder. The neurological disorder can, e.g., be a degenerative disorder, such as Parkinson's, Essential Tremor, Epilepsy, and Huntington's, or a brain injury or infarction, such as stroke.

The method comprises intravascularly delivering a first electrical lead within the head of the patient. For example, the intravascular lead can be delivered through the circulatory system, such as through a cerebral vein or artery. A suitable access point to the circulatory system, such as that made within the jugular vein, carotid artery, femoral vein, or femoral artery, can be used to introduce the intravascular lead into the circulatory system. Alternatively, the intravascular lead can be delivered through the ventricular system, e.g., up the spinal canal and into the ventricular cavity deep within the patient's brain.

The method further comprises non-vascularly delivering a second electrical lead within the head of the patient, e.g., through an opening within the cranium created by drilling a burr hole or performing a craniotomy. The method further comprises placing the intravascular and non-vascular leads adjacent brain tissue, (e.g., cortical brain tissue or deep brain tissue). The vascular lead can remain within a vessel, thereby providing indirect contact with the brain tissue, or can be deployed through a puncture made within the vessel into direct contact with the brain tissue. The leads can be acutely, sub-chronically or chronically placed adjacent the brain tissue.

Although the invention should not be so limited in its broadest aspects, use of intravascular leads provides for a minimally invasive delivery means where the affected brain tissue region is adjacent a navigatable vessel, whereas the use of non-vascular leads provides a delivery means where the affected brain tissue region is not adjacent a navigatable vessel. The leads can then be used to stimulate and/or record signals from the brain tissue.

Optionally, the method further comprises electrically coupling the proximal ends of the leads to a stimulation source and/or recorder, which may be implanted within the patient's body external to the vasculature system. Using the leads, the brain tissue can then be stimulated and/or recorded in order to treat the neurological disorder.

BRIEF DESCRIPTION OF THE DRAWINGS

The drawings illustrate the design and utility of preferred embodiment(s) of the invention, in which similar elements are referred to by common reference numerals. In order to better appreciate the advantages and objects of the invention, reference should be made to the accompanying drawings that illustrate the preferred embodiment(s). The drawings, however, depict the embodiment(s) of the invention, and should not be taken as limiting its scope. With this caveat, the embodiment(s) of the invention will be described and explained with additional specificity and detail through the use of the accompanying drawings in which.

DETAILED DESCRIPTION OF THE PREFERRED EMBODIMENTS

Figure 1:
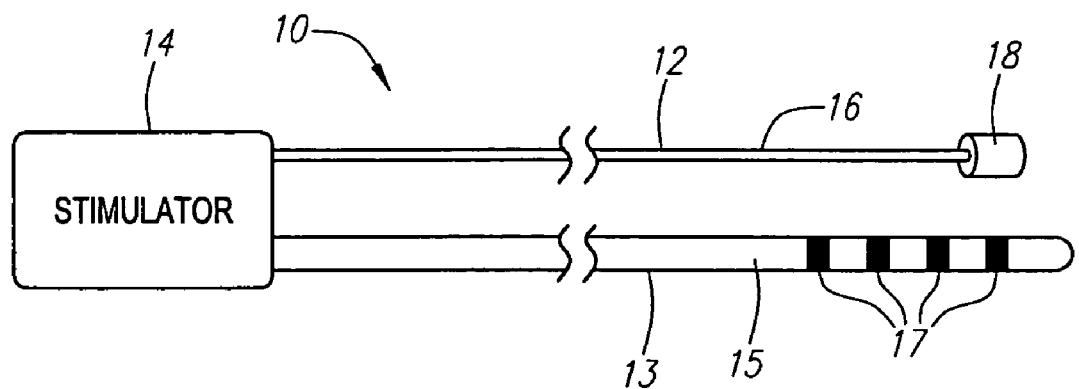
FIG. 1 is a plan view of an intravascular brain stimulation system constructed in accordance with a preferred embodiment of the present invention.

Referring now to FIG. 1, an intravascular brain stimulation system 10 constructed in accordance with one preferred embodiment of the present invention is shown. In its simplest form, the stimulation system 10 generally comprises a first stimulation lead 12 configured to be intravascularly implanted within a selected region of a patient's brain, a second stimulation lead 13 configured to be non-vascularly implanted within a selected region of the patient's brain, and an implantable electrical stimulation source 14 configured for delivering stimulation energy to the respective stimulation leads 12 and 13. In alternative embodiments, multiple intravascular leads 12 and/or multiple non-vascular leads 13 can be provided.

The intravascular lead 12 comprises a flexible electrically conductive signal wire 16 and a single electrode 18 mounted at the distal end of the wire 16 using suitable connection means, such as soldering or welding. In the illustrated embodiment, the electrode 18 is cylindrically shaped and has a size that allows it to be delivered through a delivery catheter. The wire 16 comprises an electrically conductive core with an outer insulative layer. The length of the wire 16 is preferably sized to extend from the selected stimulation site in the brain to the implant location of the stimulation source 14. For example, if the stimulation source 14 is to be implanted in the chest region of the patient, the length of the wire 16 may be in the range of 50 cm to 100 cm. If, however, the stimulation source 14 is to be implanted in the abdomen or groin area of the patient, the length of the wire 16 may be in the range of 150 cm to 300 cm. The electrode 18 is composed of a biocompatible and electrically conducting material, such as copper alloy, platinum, stainless steel, or nitinol. The electrically conducting material of the electrode 18 can be further coated with platinum-iridium or gold to improve its conduction properties, biocompatibility, and radiopacity. To prevent blood clotting, the electrode lead 12 can be optionally coated with a non-thrombogenic agent.

Figure 2:
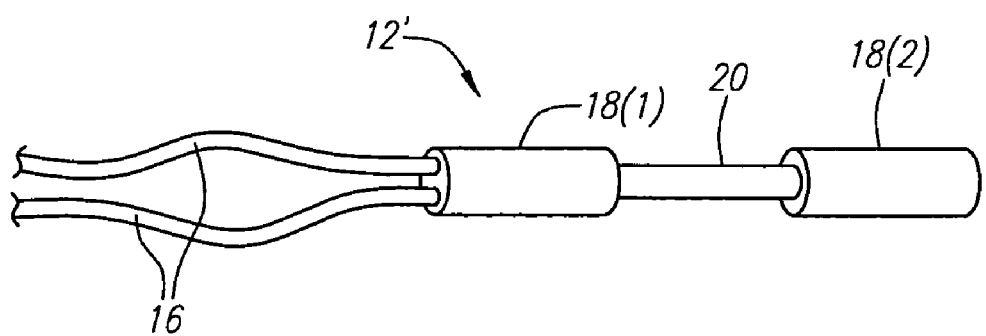
FIG. 2 is a perspective view of an alternative embodiment of an intravascular stimulation lead that can be used in the system of FIG. 1.

Referring to FIG. 2, an alternative embodiment of a stimulation electrode lead 12' is shown. The stimulation lead 12' is similar to the previously described stimulation lead 12, with the exception that it comprises a pair of electrodes 18 (a proximal electrode 18(1) and a distal electrode 18(2)) and a pair of signal wires 16 respectively coupled to the pair of electrodes 18. The electrode pair 18 can be suitably formed, e.g., by mounting a pair of ring electrodes around an electrically insulative cylindrical core 20, or by coating the cylindrical core 20 with electrically conductive material. The signal wires 16 extend through the cylindrical core 20 into contact with the respective electrodes 18(1) and 18(2). Thus, it can be appreciated that the stimulation lead 12', by itself, can be operated in a bipolar mode. This is in contrast to the stimulation lead 12, which can be operated in a monopolar mode, or alternatively, can be operated in a bipolar mode in conjunction with another stimulation lead 12, as will be described in further detail below.

It should be noted that the intravascular stimulation lead 12(1) have a different structure than that illustrated in FIG. 1. For example, the intravascular stimulation lead 12(1) may alternatively or optionally have a stent electrode, arrayed electrode structure, basket electrode structure, inflatable electrode structure, helical electrode structure, etc., may take the form of a guidewire or catheter, and may have optional blood occlusion features, such as a balloon or RF ablation electrode, the details of which are disclosed in U.S. patent application Ser. No. 10/744,319, entitled "Method of Intravascularly Delivering Stimulation Leads into the Brain", which is expressly incorporated herein by reference.

The non-vascular stimulation lead 13 comprises a flexible tubular body 15 and a plurality of ring electrodes 17 (in this case, four) mounted to the distal end of the tubular body 15. Signal wires (not shown) extend through the tubular body 15 into electrical connection with the respective ring electrodes 17. The tubular body 15 may comprise a lumen through which a stylet can be introduced to facilitate delivery of the non-vascular lead 13 through brain tissue. Non-vascular stimulations 13 are standard in the industry and may be obtained from Medtronic, Inc., located in Minneapolis, Minn.

Referring back to FIG. 1, the implantable stimulation source 14 is designed to deliver electrical pulses to the stimulation leads 12 and 13 in accordance with programmed parameters. In the preferred embodiment, the stimulation source 14 is programmed to output electrical pulses having amplitudes varying from 0.1 to 20 volts, pulse widths varying from 0.02 to 1.5 milliseconds, and repetition rates varying from 2 to 2500 Hertz. In the illustrated embodiment, the stimulation source 14 takes the form of a totally self-contained generator, which once implanted, may be activated and controlled by an outside telemetry source, e.g., a small magnet. In this case, the pulse generator has an internal power source that limits the life of the pulse generator to a few years, and after the power source is expended, the pulse generator must be replaced. Generally, these types of stimulation sources 14 may be implanted within the chest or abdominal region beneath the skin of the patient.

Alternatively, the implantable stimulation source 14 may take the form of a passive receiver that receives radio frequency (RF) signals from an external transmitter worn by the patient. In this scenario, the life of the stimulation source 14 is virtually unlimited, since the stimulation signals originate from the external transmitter. Like the self-contained generators, the receivers of these types of stimulation sources 14 can be implanted within the chest or abdominal region beneath the skin of the patient. The receivers may also be suitable for implantation behind the ear of the patient, in which case, the external transmitter may be worn on the ear of the patient in a manner similar to that of a hearing aid. Stimulation sources, such as those just described, are commercially available from Medtronic, Inc., located in Minneapolis, Minn. Further details regarding the construction of a stimulation source for the purpose of treating neurological disorders is disclosed in U.S. Pat. No. 5,716,377, which is expressly incorporated herein by reference.

The stimulation source 14 may be connected to the stimulation leads 12 and 13 in any one of a variety of manners. For example, each stimulation lead 12/13 can be connected in a unipolar arrangement or a bipolar arrangement, or the stimulation leads 12/13 can be connected together in a bipolar arrangement, further details of which are described in U.S. patent application Ser. No. 10/744,319, which has previously be incorporated herein by reference.

In optional embodiments, the stimulation source 14 provides automated feedback for recording and stimulation to control such neurological disorders as Epileptic seizures.

Further details on the use of feedback to control Epileptic seizures and other disorders are disclosed in U.S. Pat. No. 5,716,377, which has previously been incorporated herein by reference, and U.S. Pat. No. 6,360,122, which is expressly incorporated herein by reference. In other optional embodiments, a dedicated brain signal recorder (not shown) can be connected to one or more electrode leads. In this case, the electrode lead(s) connected to the dedicated recorder will not be a stimulation lead, but instead, will act as a recording lead.

Having described the structure of the intravascular brain stimulation system 10, a preferred method of installing it within a patient's body in order to treat a diagnosed neurological disorder within the brain will now be described. As will be described in further detail below, the stimulation lead 12 will be intravascularly introduced within the patient's head adjacent a selected brain region and the stimulation lead 13 will be non-vascularly introduced within the patient's head through, e.g., a burr hole drilled within the patient's cranium, or by performing a craniotomy.

The routing and placement of the brain stimulation system 10 will ultimately depend on the portion of the brain that is to be treated. For example, the cortex of the brain or the deep brain can be electrically stimulated to provide post-stroke rehabilitation (from hemorrhagic stroke, ischemic stroke or head/brain trauma), Parkinson's Disease, Essential Tremor, Huntington's Disease, Alzheimer's Disease, Epilepsy, depression, obsessive compulsive disorder, schizophrenia, and neuropathic pain. Any lobe of the cortex or deep brain can be stimulated. Preferably, for the cortical region of the brain, the motor strip, sensor strip, and premotor cortex should be stimulated. For the deep brain region, the anterior thalamus, ventrolateral thalamus (Thal), internal segment of globus pallidus (GPi), substantia nigra pars reticulata (SNr), subthalamic nucleus (STN), external segment of globus pallidus (GPe), neostriatum, cingulate, and cingulate gyrus should be stimulated.

The spheno palatine ganglion (SPG), which can control the amount of blood flow to the brain and the permeability of the blood brain barrier, may also be stimulated, e.g., to hyperperfuse a hemisphere of the brain damaged as a result of an ischemic event, such as a stroke, or to help metabolize amlyoid plaques caused by Alzheimer's Disease and prevent the occurrence of vaso-spasms, both achieved through increased blood flow to the brain. Lastly, the SPG can be stimulated to facilitate the opening of the blood-brain barrier, enabling better uptake of drugs to the brain. These drugs could be delivered in a variety of methods (e.g. orally, intravenously, or via direct injection into the penumbra) and could be used to treat a variety of neurologically related maladies (stroke, epilepsy, Parkinson's, tumors, essential tremor, Alzheimer's, etc.).

The intravascular lead 12 can be delivered to any one of a number of vessels in order to place the active portion of the stimulation lead adjacent the cortical tissue to be stimulated. Examples of veins providing access to the cortex include the superior sagittal sinus, any of the superior cerebral veins branching from the superior sagittal sinus (e.g., the lacuna, frontopolar vein, anterior frontal vein, posterior frontal vein, precentral vein, central vein, anterior parietal vein, posterior parietal vein, and occipital vein), superior sylvian vein, vein of Labbe, vein of Trolard, inferior sagittal sinus, and any inferior cerebral veins branching off of the inferior sagittal sinus, transverse sinus, and meningeal sinus. Examples of arteries providing access to the cortex include any of the branches off of the external carotid, maxillary, or meningeal arteries.

Examples of veins providing access to the deep brain include the inferior sagittal sinus, pericallosal sinus, cavernous sinus, sphenoid sinus, temperal basal vein, and occipital veins. Examples of arteries providing access to the deep brain include any branches off of the internal carotid or vertebral arteries. Examples of veins providing access to the SPG include the superficial temporal veins and the facial vein. Examples of arteries providing access to the SPG include the maxillary artery, descending palatine artery, and facial artery.

The jugular and femoral veins can be used as intrasvascular access points from which stimulation leads can be delivered to the above-described veins, and the carotid or femoral arteries can be used as intravascular access points from which the stimulation leads can be delivered to the above-described arteries.

Of course, in those brain regions that are not adjacent one of these blood vessels, or is otherwise adjacent a blood vessel that is not navigatable by the intravascular lead 12, such brain regions will have to be reached by non-vascular means, e.g., by epidurally or subdurally placing the stimulation lead 13 along the cortex for cortical simulation, or by penetrating the parenchyma for deep brain stimulation.

Thus, it can be appreciated that the combination of intravascular and non-vascular placement of the stimulation leads 12/13 lends itself well to procedures that involve multiple brain regions, at least one of which is adjacent a navigatable blood vessel and at least one of which is not adjacent a navigatable blood vessel.

Figure 3:
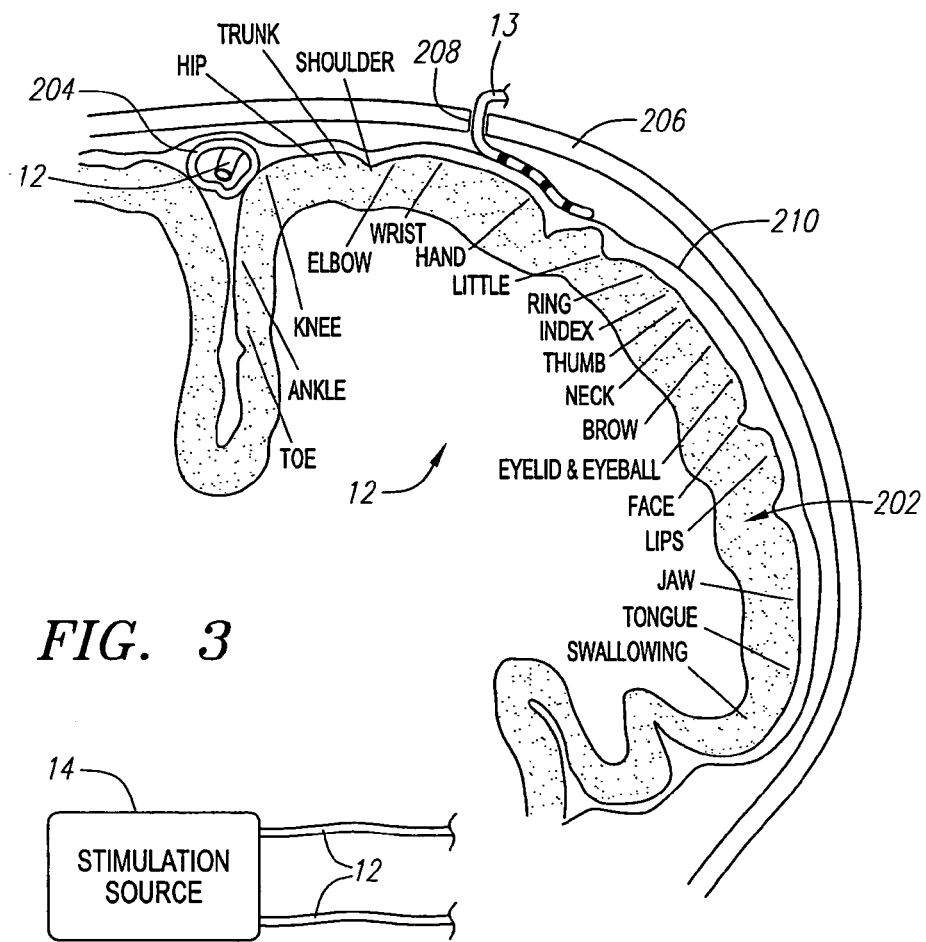
FIG. 3 is an anterior view of one hemisphere of a patient's brain, particularly illustrating installation of the brain stimulation system of FIG. 1 therein in order to treat hemiparetic patient.

For example, FIG. 3 illustrates a patient's brain 200, and in particular, the sagittal sinus 204 in relation to the cortical brain regions 202 used to control the voluntary movement of various parts of the patient's body. As can be seen, the cortical brain regions 202 that control the leg regions of the patient, including the toes, ankle, knee, and hip, are near the sagittal sinus 204, whereas the cortical brain regions 202 that control the remaining portions of the patient are not adjacent the sagittal sinus 204. In the case of a hemiparetic patient who has loss of function in both the hand and foot, it may be preferred to electrically stimulate the hand motor cortex area of the brain 200 using an epidurally placed non-vascular stimulation lead 13, since no major blood vessel is in juxtaposition to that area, whereas it may be preferred to electrically stimulate the foot motor cortex area of the brain 200 using a intravascular stimulation lead 12 placed in the sagittal sinus 204, which sits directly on top of that functional region of the brain.

With the use of a guide wire, delivery catheter, and/or guide sheath (all not shown), the stimulation lead 12 can be intravascularly delivered into the sagittal sinus 204 adjacent the leg controlling region of the brain from a remote access site, such as the inner jugular vein or femoral vein (not shown). The stimulation lead 12 may be located within the sagittal sinus 204, such that stimulation can be indirectly applied to the tissue of the affected brain region, or alternatively, can be inserted through a puncture within the sagittal sinus 204 in direct contact with the brain tissue with the aid of a stylet. The access site into the vasculature will ultimately depend on the selected implantation site of the stimulation source 14. For example, if the stimulation source 14 is to be implanted within the chest or clavical region, or behind the ear, of the patient, the jugular vein should be selected as the access point. If, on the other hand, the stimulation source 14 is to be implanted within the abdominal or groin region of the patient, the femoral vein should be selected as the access point. Further details on the use of guidewires, delivery catheters, and guide sheaths to intravascularly deliver stimulation leads into indirect or direct contact with brain tissue is described in U.S. patent application Ser. No. 10/744,319, entitled "Method of Intravascularly Delivering Stimulation Leads into the Brain," which has previously been incorporated herein by reference. Details on the intravascular delivery of stimulation leads that take the form of a guidewires or catheters are also disclosed therein. The non-vascular lead 13 is introduced through a burr hole 208 made through the cranium 206, along the dural layer 210 into contact with the brain region that controls the hand in a standard manner. Of course, other stimulation leads 12/13 can be intravascularly or non-vascularly delivered into the brain 200 as needed.

After the stimulation leads 12/13 have been deployed within the brain 200, the proximal ends of the implanted stimulation leads 12/13 will remain outside of the patient's body after the stimulation deployment process is completed, and in particular, the intravascular stimulation lead 12 will extend from the vascular access point, e.g., the internal jugular vein or femoral vein, and the non-vascular stimulation lead 13 will extend from the burr hole 208. These exposed ends of the stimulation leads 12/13 can be subcutaneously routed a short distance to the clavical or chest region or behind the ear of the patient (in this case where the jugular vein is the access point) or the abdominal or groin region of the patient (in the case where the femoral vein is the access point), where they can be coupled to the implanted stimulation source 14, as illustrated in FIG. 3. Alternatively, the stimulation source 14 may not be implanted, but rather located exterior to the patient. e.g., during a non-chronic procedure. The stimulation leads 12/13 can either be coupled in a monopolar arrangement or a bipolar arrangement. Depending on the nature of the neurological disorder and goals of the operation, the stimulation leads 12/13 may be left within the brain either acutely (i.e., only during an operation and then removed after the operation has been completed), chronically, or sub-chronically (i.e., less than six months).

Figure 4:
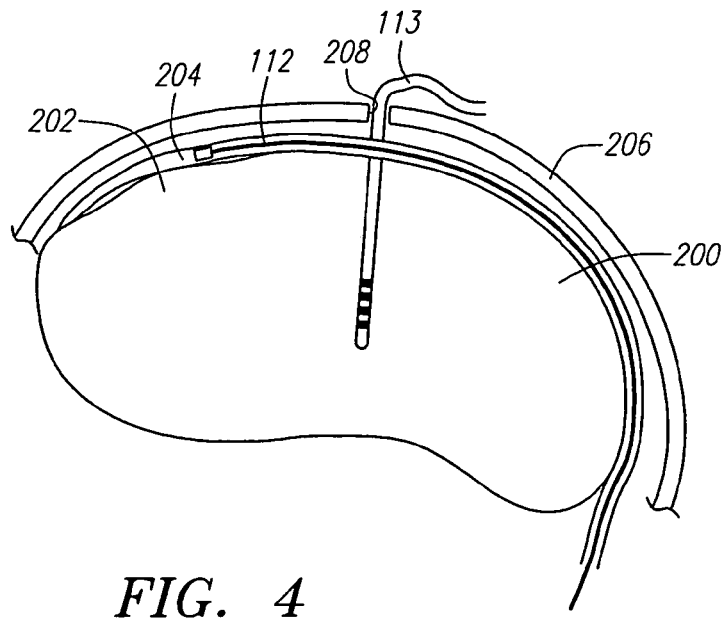
FIG. 4 is a lateral view of a patient's brain, particularly illustrating installation of the brain stimulation system of FIG. 1 therein in order to record the onset of an epileptic seizure and to stimulate a the patient out of an epileptic seizure.

The stimulation system 10 can also be used to treat epilepsy. For example, referring to FIG. 4, lead 12, in the form of a recording lead, can be intravascularly introduced along the sagittal sinus 204 in order to record brain signals from the cortex 202 of the brain 200, so that the onset of a seizure can be predicted. The stimulation lead 13 can be introduced through a bore hole 208 in the cranium 206 and through the parenchyma of the brain in order to provide deep brain stimulation in order to stimulate the patient out of the seizure. The leads 12/13 can be routed in the same manner described above, with the exception, that they will be connected to an implanted combined stimulation source/recorder.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A medical method performed on a patient, comprising:
   intravascularly delivering a first electrical lead within the head of the patient;
   non-vascularly delivering a second electrical lead within the head of the patient;
   placing one of the first electrical lead and the second electrical lead adjacent a first brain tissue region;
   placing another of the first electrical lead and the second electrical lead adjacent a second brain tissue region;
   stimulating the first brain tissue region with the one of the first electrical lead and the second electrical lead to treat a neurological disorder of the patient; and
   recording brain signals at the second brain tissue region with the other of the first electrical lead and the second electrical lead to monitor the neurological disorder.

2. The method of claim 1, wherein the neurological disorder is a degenerative disorder.

3. The method of claim 1, wherein the neurological disorder is a brain infarction.

4. The method of claim 1, wherein the first electrical lead is introduced into the head via the circulatory system.

5. The method of claim 1, wherein the first electrical lead is introduced into the head via the ventricular system.

6. The method of claim 1, wherein the first electrical lead is placed in direct contact with the brain tissue.

7. The method of claim 1, wherein the first electrical lead is placed in indirect contact with the brain tissue.

8. The method of claim 1, wherein the first electrical lead is placed adjacent cortical brain tissue, and the second electrical lead is placed adjacent deep brain tissue.

9. The method of claim 1, wherein the first electrical lead is placed adjacent deep brain tissue, and the second electrical lead is placed adjacent cortical brain tissue.

10. The method of claim 1, further comprising:
    electrically connecting the one of the first electrical lead and the second electrical lead to a stimulation source; and
    electrically connecting the other of the first electrical lead and the second electrical lead to a recorder.

11. The method of claim 10, further comprising implanting the stimulation source and the recorder within the patient.

12. A medical method performed on a patient, comprising:
    delivering a first electrical lead within the head of the patient via a blood vessel;
    delivering a second electrical lead within the head of the patient via an opening in an cranium of the patient; and
    placing one of the first electrical lead and the second electrical lead adjacent a first brain tissue region;
    placing another of the first electrical lead and the second electrical lead adjacent a second brain tissue region;
    stimulating the first brain tissue region with the one of the first electrical lead and the second electrical lead to treat a neurological disorder of the patient; and
    recording brain signals at the second brain tissue region with the other of the first electrical lead and the second electrical lead to monitor the neurological disorder.

13. The method of claim 12, wherein the neurological disorder is a degenerative disorder.

14. The method of claim 12, wherein the neurological disorder is a brain infarction.

15. The method of claim 12, wherein the blood vessel is a vein.

16. The method of claim 12, wherein the blood vessel is an artery.

17. The method of claim 12, wherein the first electrical lead is placed in direct contact with the brain tissue.

18. The method of claim 12, wherein the first electrical lead is placed in indirect contact with the brain tissue.

19. The method of claim 12, wherein the first electrical lead is placed adjacent cortical brain tissue, and the second electrical lead is placed adjacent deep brain tissue.

20. The method of claim 12, wherein the first electrical lead is placed adjacent deep brain tissue, and the second electrical lead is placed adjacent cortical brain tissue.

21. The method of claim 12, further comprising:
electrically connecting the one of the first electrical lead and the second electrical lead to a stimulation source; and
electrically connecting the other of the first electrical lead and the second electrical lead to a recorder.

22. The method of claim 21, further comprising implanting the stimulation source and the recorder within the patient.

23. The method of claim 1, wherein the one of the first electrical lead and the second electrical lead is the second electrical lead, and the other of the first electrical lead and the second electrical lead is the first electrical lead.

24. The method of claim 23, wherein the first electrical lead records the brain signals from within the sagittal sinus of the patient.

25. The method of claim 1, wherein the neurological disorder is epilepsy.

26. The method of claim 1, wherein the brain signals recorded at the second brain tissue region by the other of the first electrical lead and the second electrical lead indicate the onset of a seizure, and the one of the first electrical lead and the second electrical lead stimulates the first brain tissue region to stop the seizure.

27. The method of claim 12, wherein the one of the first electrical lead and the second electrical lead is the second electrical lead, and the other of the first electrical lead and the second electrical lead is the first electrical lead.

28. The method of claim 27, wherein the first electrical lead records the brain signals from within the sagittal sinus of the patient.

29. The method of claim 12, wherein the neurological disorder is epilepsy.

30. The method of claim 12, wherein the brain signals recorded at the second brain tissue region by the other of the first electrical lead and the second electrical lead indicate the onset of a seizure, and the one of the first electrical lead and the second electrical lead stimulates the first brain tissue region to stop the seizure.

* * * * *